(12) United States Patent
Akira et al.

(10) Patent No.: US 7,371,921 B2
(45) Date of Patent: May 13, 2008

(54) NONHUMAN ANIMAL MODEL NON-RESPONSIVE TO MYCOPLASMA-ORIGIN LIPOPROTEIN/LIPOPEPTIDE

(75) Inventors: Shizuo Akira, Takatsuki (JP); Osamu Takeuchi, Mino (JP)

(73) Assignee: Japan Science and Technology Agency, Kawaguchi-Shi, Saitama (JP)

( * ) Notice: Subject to any disclaimer, the term of this patent is extended or adjusted under 35 U.S.C. 154(b) by 493 days.

(21) Appl. No.: 10/343,388

(22) PCT Filed: Jul. 31, 2001

(86) PCT No.: PCT/JP01/06555

§ 371 (c)(1),
(2), (4) Date: Jan. 30, 2003

(87) PCT Pub. No.: WO02/09508

PCT Pub. Date: Feb. 7, 2002

(65) Prior Publication Data

US 2003/0149999 A1 Aug. 7, 2003

(30) Foreign Application Priority Data

Jul. 31, 2000 (JP) ............................. 2000-232451

(51) Int. Cl.
*A01K 67/027* (2006.01)
*G01N 33/00* (2006.01)
*C12N 5/00* (2006.01)
*C12N 5/02* (2006.01)
*C12N 5/06* (2006.01)
*C12N 5/16* (2006.01)
*C12N 5/10* (2006.01)

(52) U.S. Cl. ............................. 800/18; 800/3; 435/325; 435/340; 435/355

(58) Field of Classification Search ................ None
See application file for complete search history.

(56) References Cited

OTHER PUBLICATIONS

Muhlradt. PF et al, 1998, Infection and Immunity, 66:4804-4810.*
Brightbill, HD et al, 1999, Science, 285:732-735.*
Prelle, K. 1999, Establishment of pluripotent cell lines from vertebrate species-present status and future prosopects, Cells Tissues Organs, vol. 165, pp. 220-236.*
Moreadith, 1997, Gene targeting in embryonic stem cells : the new physiology and metabolism, Journal of Molecular Medicine, vol. 75, pp. 208-216.*
Katsuaki Hoshino, et al., Cutting Edge:Toll-Like Receptor 4 (TLR4)-Deficient Mice Are Hyporesponsive to Lipopolysaccharide:Evidence for TLR4 as the *Lps* Gene Product, The Journal of Immunology, 3749-3752 (1999).
Bruno Lemaitre, et al., The Dorsoventral Regulatory Gene Cassette *spätzle/Toll/cactus* Controls the Potent Antifungal Response in *Drosophila* Adults, Cell. 86:973-983, (1996).
Nicholas J. Gay, et al., *Drosophila* Toll and IL-1 Receptor, Nature, 351:355-356 (1991).
Marcia P. Belvin, et al., A Conserved Signaling Pathway:The *Drosophila* Toll-Dorsal Pathway, Annu. Rev. Cell Dev. Biol, 12:393-416 (1996).
Luke A. J. O'Neill et al., Signal Transduction Pathways Activated By The IL-1 Receptor Family:Ancient Signalhng Machinery In Mammals, Insects, And Plants, J. Leukoc. Biol. 63:650-657, (1998).
Rusian Medzhitov, et al., A Human Homologue Of The *Drosophila* Toll Protein Signals Activation of Adaptive Immunity, Nature, 388:394-397, (1997).
Fernando L. Rock, et al., A Family Of Human Receptors Structurally Related To *Drosophila* Toll, Proc. Natl. Acad. Sci. USA, 95:588-593 (1998).
Preet M. Chaudhary, et al., Cloning and Characterization of Two Toll/Interleukin-1 Receptor-Like Genes TIL3 and TIL4:Evidence for a Multi-Gene Receptor Family in Humans, Blood, 91:4020-4027 (1998).
O. Takeuchi, et al., TLR6: A Novel Member of an Expanding Toll-Like Receptor Family, Gene, 231:59-65 (1999).
Marta Muzio, et al., The Human Toll Signaling Pathway:Divergence of Nuclear Factor kB and JNK/SAPK Activation Upstream of Tumor Necrosis Factor Receptor-associated Factor 6 (TRAF6), J. Exp. Med., 187:2097-2101 (1998).
Rusian Medzhitov, et al., MyD88 Is An Adaptor Protein In The hToll/IL-1 Receptor Family Signaling Pathways, Mol. Cell, 2:253-258 (1998).
Rusian Medzhitov, et al., Innate Immunity:The Virtues of a nonclonal System of Recognition, Cell, 91:295-298 (1997).

(Continued)

*Primary Examiner*—Valarie Bertoglio
(74) *Attorney, Agent, or Firm*—Morgan & Finnegan LLP

(57) ABSTRACT

An object of the present invention is to provide a non-human animal model unresponsive to a mycoplasma-derived lipoprotein/lipopeptide, and a method for screening an inhibitor or a promoter for a response to a mycoplasma-derived lipoprotein with the use of the non-human animal model. A non-human animal model whose function of a gene that encodes a protein such as TLR6 that specifically recognizes a mycoplasma-derived lipoprotein is deficient on its chromosome, for example, a TLR6 knockout mouse, is generated. With the use of the non-human animal model unresponsive to a mycoplasma-derived lipoprotein or an immune cell such as a macrophage derived from the non-human animal model, a subject material and a mycoplasma-derived lipoprotein, a response to a mycoplasma-derived lipoprotein in the non-human animal model or the immune cell is measured/evaluated, and then an inhibitor or a promoter for a response to that is screened.

2 Claims, 3 Drawing Sheets

OTHER PUBLICATIONS

R.J. Ulevitch, et al., Receptor-Dependent Mechanisms of Cell Stimulation by Bacterial Endotoxin, Annu. Rev. Immunol. 13:437-57 (1995).
Samuel D. Wright, et al., CD14, a Receptor for Complexes of Lipopolysaccharide (LPS) and LPS Bindin Protein, Science, 249:1431-1433 (1990).
Osamu Takeuchi, et al., Differential Roles of TLR2 and TLR4 in Recognition of Gram-Negative and Gram-Positive Bacterial Cell Wall Components, Immunity, 11:443-451 (1999).
Taro Kawai, et al., Unresponsiveness of MyDS88-Deficient Mice to Endotoxin, Immunity, 11:115-122 (1999).
Takeuchi et al, International Immunology, vol. 13, No. 7, pp. 933-940, Jul. 2001.
Takeuchi et al, The Journal of Immunology, vol. 164, No. 2, pp. 554-557, Jan. 15, 2000.
Liu et al, Cell, vol. 95, pp. 269-277, Oct. 16, 1998.
Osamu Takeuchi, Akira Shizuo, "Toll-like Receptor Knockout Mice", Saibo Kogaku, Apr. 22, 2000, vol. 19, No. 5, pp. 767-774 IPER for PCT JP01/06555 only.
Takeuchi et al., International Immunology, vol. 12, No. 1, pp. 113-117, Jan. 2000.
Galanos et al., Journal of Endotoxin Research, vol. 6, No. 6, pp. 471-476, Jun. 2000.
Sugawara et al., Microbiol. Immunol., vol. 47, No. 5, pp. 327-336, May 2003.
European Patent Office, Supplementary Partial European Search Report for EP 01 95 3338, dated Oct. 10, 2005 (cover sheet from European Patent Office dated Oct. 24, 2005) (total of 4 pages).

* cited by examiner

NONHUMAN ANIMAL MODEL NON-RESPONSIVE TO MYCOPLASMA-ORIGIN LIPOPROTEIN/LIPOPEPTIDE

TECHNICAL FIELD

The present invention relates to a non-human animal model unresponsive to a mycoplasma-derived lipoprotein/lipopeptide, whose function of a gene that encodes a protein such as TLR6 that specifically recognizes a mycoplasma-derived lipoprotein/lipopeptide is deficient on its chromosome, and a method for screening an inhibitor or a promoter for a response to a mycoplasma-derived lipoprotein/lipopeptide with the use of the non-human animal model, etc.

BACKGROUND ART

It has been known that the Toll gene is required to control dorsoventral patterning during the embryonic development of Drosophila (Cell 52, 269-279, 1988; Annu. Rev. Cell Dev. Biol. 12, 393-416, 1996), and for antifungal immune responses in adult fly (Cell 86, 973-983, 1996). It has been clarified that the Toll is a type I transmembrane receptor with an extracellular domain containing leucine-rich repeat (LRR) and that its cytoplasmic domain shows high homology to that of a mammalian interleukin-1 receptor (IL-1R) (Nature 351, 355-356, 1991; Annu. Rev. Cell Dev. Biol. 12, 393-416, 1996; J. Leukoc. Biol. 63, 650-657, 1998).

Recently, mammalian homologs of Toll, designated as Toll-like receptors (TLRs), have been identified, and so far, six families including TLR2 and TLR4 have been reported (Nature 388, 394-397, 1997; Proc. Natl. Acad. Sci. USA 95, 588-593, 1998; Blood 91, 4020-4027, 1998; Gene 231, 59-65, 1999). It has been known that the TLR families, as in the case of the IL-1R mentioned above, recruit IL-1R-associated kinase (IRAK) through the adapter protein MyD88 and activate TRAF6, and then activate NF-êB in the downstream (J. Exp. Med. 187, 2097-2101, 1998; Mol. Cell 2, 253-258, 1998; Immunity 11, 115-122, 1999). Further, the role of the TLR families in mammals is also believed to participate in congenital immune recognition as pattern recognition receptors (PRRs), which recognize bacterial cell common structures (Cell 91, 295-298, 1997).

It has been reported that one of such pathogen-associated molecular patterns (PAMPs) to be recognized by the PRRs is a lipopolysaccharide (LPS), a major component of the outer membrane of Gram negative bacteria (Cell 91, 295-298, 1997), that the LPS stimulates host cells and makes them produce various proinflammatory cytokines including TNFá, IL-1, and IL-6 (Adv. Immunol. 28, 293-450, 1979; Annu. Rev. Immunol. 13, 437-457, 1995), and that the LPS captured by LPS-binding protein (LBP) is delivered to CD14 on the cell surface (Science 249, 1431-1433, 1990; Annu. Rev. Immunol. 13, 437-457, 1995). The inventors of the present invention have constructed TLR4 knockout and TLR2 knockout mice, and have reported that the TLR4 knockout mouse is unresponsive to LPS, a major component of the outer membrane of Gram negative bacteria mentioned above (J. Immunol. 162, 3749-3752, 1999) and that a macrophage of the TLR2 knockout mouse decreased the reactivity of the TLR2 knockout mouse to the cell wall of Gram positive bacteria and peptidoglycan, a component of the cell wall (Immunity, 11, 443-451, 1999).

On the other hand, Mycoplasma is the smallest microorganism that can self-propagate, and is biologically classified into bacteria. However, unlike other bacteria, Mycoplasma does not have a cell wall, and therefore, it shows polymorphology and is unresponsive to cell wall synthesis inhibitors such as penicillin and cephem. Though there are seven kinds of Mycoplasma which are often separated from human, only *Mycoplasma pneumoniae* shows apparent pathogenicity and is known to cause respiratory infections such as upper respiratory infection, bronchitis and pneumonia. Recently, the present inventors have revealed that a bacterial cell component such as a mycoplasma-derived lipoprotein/lipopeptide causes vital reaction via TLR2 and MyD88 signaling pathways (J. Immunol. 164, 554-557, 2000). However, a protein that specifically recognizes a mycoplasma-derived lipoprotein/lipopeptide has been unknown, and consequently, the molecular mechanism that a mycoplasma-derived lipoprotein/lipopeptide activates immune cells has not been elucidated sufficiently.

Though in vivo responses to bacterial cell components are expected to vary depending on the difference of expression levels of each TLR on the cell surface, the contribution of individual members of the TLR family to signaling by bacterial cell components' stimuli in vivo remains to be elucidated. In addition, though it is known that a water-insoluble lipoprotein/lipopeptide that is present on a biomembrane etc. activates immune cells, a protein that specifically recognizes a mycoplasma-derived lipoprotein/lipopeptide has been unknown. An object of the present invention is to provide a non-human animal model unresponsive to a mycoplasma-derived lipoprotein/lipopeptide, whose function of a gene that encodes a protein that specifically recognizes a mycoplasma-derived lipoprotein/lipopeptide is deficient on its chromosome, particularly a non-human animal whose function of the TLR6 gene is deficient on its chromosome, which is useful for elucidating the contribution of individual members of the TLR family to signaling by stimulation with a mycoplasma-derived lipoprotein/lipopeptide in vivo, especially the role of TLR6 in vivo, and a method for screening an inhibitor or a promoter for a response to a mycoplasma-derived lipoprotein/lipopeptide with the use of the non-human animal model.

As aforementioned, as to TLR family in mammals, which is involved in congenital immune recognition as a pattern recognition receptor which recognizes bacterial cell common structures, six members of them (TLR1-6) have been reported (Nature 388, 394-397, 1997; Proc. Natl. Acad. Sci. USA, 95, 588-593, 1998; Gene 231, 59-65, 1999). However, a receptor that specifically recognizes a mycoplasma-derived lipoprotein/lipopeptide has been unknown. The present inventors have generated TLR6 konckout mice as follows: cDNA of TLR6 which had been identified was isolated from mouse gene library; a genetic site containing an intracellular domain and a transmembrane domain of the TLR6 gene was replaced with a neomycin-resistant gene, and a HSV-tk gene was introduced into each C-terminal side respectively, and ES cell clones doubly resistant to G418 and ganciclovir were screened; the ES cell clones were injected into blastocysts of C57BL/6 mice; TLR6 knockout mice whose function of TLR6 genes is deficient on their chromosomes were born through the germline at the expected Mendelian ratios. Subsequently the present inventors have found that TLR6 is a receptor protein that specifically recognizes a mycoplasma-derived lipoprotein/lipopeptide by comparing/analyzing the TLR6 knockout mice, wild-type mice and TLR2 knockout mice, and the present invention has completed.

DISCLOSURE OF THE INVENTION

The present invention relates to a non-human animal model unresponsive to a mycoplasma-derived lipoprotein/lipopeptide, whose function of a gene that encodes a protein that specifically recognizes a mycoplasma-derived lipoprotein/lipopeptide is deficient on its chromosome (claim 1), the non-human animal model unresponsive to a mycoplasma-derived lipoprotein/lipopeptide according to claim 1, wherein the protein that specifically recognizes a mycoplasma-derived lipoprotein/lipopeptide is TLR6 (claim 2), the non-human animal model unresponsive to a mycoplasma-derived lipoprotein/lipopeptide according to claim 1 or 2, wherein the non-human animal is a rodent (claim 3), the non-human animal model unresponsive to a mycoplasma-derived lipoprotein/lipopeptide according to claim 3, wherein the rodent is a mouse (claim 4), the non-human animal model unresponsive to a mycoplasma-derived lipoprotein/lipopeptide according to claim 4, wherein the mouse is a TLR6 knockout mouse obtained by a process comprising the steps of: a targeting vector is constructed by replacing the whole or a part of a gene fragment of a genetic site containing an intracellular domain and a transmembrane domain of the TLR6 gene, which is obtained by a screening from a mouse gene library with the use of a probe derived from a mouse EST clone, with a plasmid having a poly A signal and a marker gene; the targeting vector is linearized and then introduced into an embryonic stem cell; the targeted embryonic stem cell deficient in TLR6 gene function is microinjected into a mouse blastocyst to construct a chimeric mouse; a heterozygous mouse was generated by mating the chimeric mouse and a wild-type mouse, and the heterozygous mice are intercrossed (claim 5).

The present invention also relates to a method for screening an inhibitor or a promoter for a response to a mycoplasma-derived lipoprotein/lipopeptide wherein with the use of an immune cell derived from the non-human animal model unresponsive to a mycoplasma-derived lipoprotein/lipopeptide according to claims 1 to 5, a subject material and a mycoplasma-derived lipoprotein/lipopeptide, a response to a mycoplasma-derived lipoprotein/lipopeptide in the immune cell is measured/evaluated (claim 6), a method for screening an inhibitor or a promoter for a response to a mycoplasma-derived lipoprotein/lipopeptide wherein with the use of the non-human animal model unresponsive to a mycoplasma-derived lipoprotein/lipopeptide according to claims 1 to 5, a subject material and a mycoplasma-derived lipoprotein/lipopeptide, a response to a mycoplasma-derived lipoprotein/lipopeptide in the non-human animal is measured/evaluated (claim 7), the method for screening an inhibitor or a promoter for a response to a mycoplasma-derived lipoprotein/lipopeptide according to claim 6 or 7, wherein in the measurement/evaluation of the response to a mycoplasma-derived lipoprotein/lipopeptide, the response is evaluated in comparison with a case using a wild-type non-human animal as a control (claim 8), the method for screening an inhibitor or a promoter for a response to a mycoplasma-derived lipoprotein/lipopeptide according to any one of claims 6 to 8, wherein the inhibitor or the promoter for a response to a mycoplasma-derived lipoprotein/lipopeptide is an inhibitor or a promoter for a mycoplasma infection (claim 9), the method for screening an inhibitor or a promoter for a response to a mycoplasma-derived lipoprotein/lipopeptide according to claim 9, wherein the mycoplasma infection is human mycoplasma pneumonia, bovine pleuropneumonia, ovine/caprine mastitis or chicken respiratory disease (claim 10), the method for screening an inhibitor or a promoter for a response to a mycoplasma-derived lipoprotein/lipopeptide according to any one of claims 6 to 8, wherein the inhibitor or the promoter for a response to a mycoplasma-derived lipoprotein/lipopeptide is an agonist or an antagonist of TLR6 (claim 11).

The present invention further relates to an inhibitor or a promoter for a response to a mycoplasma-derived lipoprotein/lipopeptide obtained by the method for screening an inhibitor or a promoter for a response to a mycoplasma-derived lipoprotein/lipopeptide according to any one of claims 6 to 11 (claim 12), the inhibitor or the promoter for a response to a mycoplasma-derived lipoprotein/lipopeptide according to claim 12, wherein the inhibitor or the promoter for a response to a mycoplasma-derived lipoprotein/lipopeptide is an inhibitor or a promoter for a mycoplasma infection (claim 13), the inhibitor or the promoter for a response to a mycoplasma-derived lipoprotein/lipopeptide according to claim 13, wherein the mycoplasma infection is human mycoplasma pneumonia, bovine pleuropneumonia, ovine/caprine mastitis or chicken respiratory disease (claim 14), the inhibitor or the promoter for a response to a mycoplasma-derived lipoprotein/lipopeptide according to claim 12, wherein the inhibitor or the promoter for a response to a mycoplasma-derived lipoprotein/lipopeptide is an agonist or an antagonist of TLR6 (claim 15).

BEST MODE FOR CARRYING OUT THE INVENTION

Figure 1:
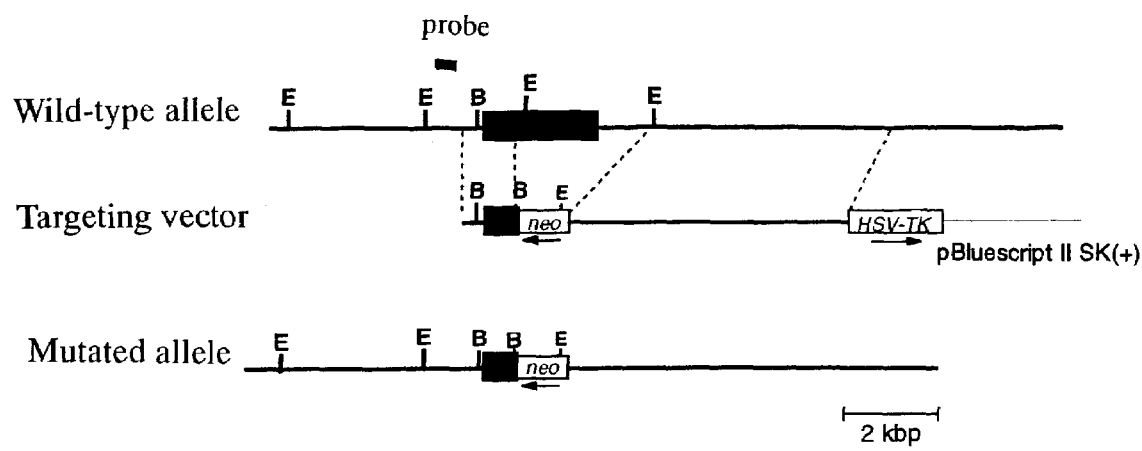
FIG. 1 is a graph showing gene maps of the TLR6 knockout mice and the wild-type mice of the present invention.

The protein that specifically recognizes a mycoplasma-derived lipoprotein/lipopeptide according to the present invention is not particularly limited as long as it is a protein that can specifically recognize a mycoplasma-derived lipoprotein/lipopeptide, and a part or the whole of TLR6 is exemplified as a specific example. The protein that specifically recognizes a mycoplasma-derived lipoprotein/lipopeptide can be prepared by known methods on the basis of its DNA sequence information etc. Further, the mycoplasma-derived lipoprotein/lipopeptide in the present invention means, other than a lipoprotein/lipopeptide derived from Mycoplasma, Mycoplasma itself or a substance treated by Mycoplasma, a lipopeptide derived from a synthetic Mycoplasma such as MALP-2, etc.

In the present invention, a non-human animal model unresponsive to a mycoplasma-derived lipoprotein/lipopeptide means a non-human animal wherein a living organism, or cells, tissues or organs which comprise a living organism show low or no reactivity specifically to the stimulation with a mycoplasma-derived lipoprotein/lipopeptide in comparison with wild-type non-human animals, that is, a non-human animal such as a mouse, a rat or a rabbit, wherein a living organism, or cells, tissues or organs which comprise a living organism show low or no reactivity specifically to the stimulation with a mycoplasma-derived lipoprotein/lipopeptide, in spite that the living organism, or the cells, the tissues, or the organs which comprise the living organism show normal reactivity to the stimulation with a lipoprotein/lipopeptide from Spirochaeta, Gram negative bacteria etc. As a specific example, a non-human animal whose function of a TLR6 gene is deficient on its chromosome, such as a TLR6 knockout mouse, is exemplified. Further, the above-mentioned stimulation with a mycoplasma-derived lipoprotein/lipopeptide includes in vivo stimulation wherein a mycoplasma-derived lipoprotein/lipopeptide is administered to a living organism, and in vitro stimulation wherein a cell separated from a living organism is made to contact with a mycoplasma-derived lipoprotein/lipopeptide.

Next, a method for generating the non-human animal model unresponsive to a mycoplasma-derived lipoprotein/lipopeptide of the present invention is explained with an example of a TLR6 knockout mouse. A gene that encodes TLR6 is screened with a gene fragment obtained from a mouse gene library by PCR or other such methods, and the screened gene that encodes the TLR6 is subcloned with a viral vector etc., then specified by DNA sequencing. The whole or a part of the gene that encodes TLR6 is replaced with pMC1 neo gene cassette or the like, and a gene such as a diphtheria toxin A fragment (DT-A) gene or a herpes simplex virus thymidine kinase (HSV-tk) gene is introduced into 3'-terminal side to construct a targeting vector.

This constructed targeting vector is linearized, and introduced into ES cells by a method such as electroporation, then the ES cells are homologously recombined, and subsequently ES cells wherein homologous recombination is caused by G418, ganciclovir (GANC) or other such antibiotics are selected from the homologous recombinants. It is preferable to confirm by Southern blotting etc. whether these selected ES cells are the object recombinants. A clone of the confirmed ES cell is microinjected into a blastocyst of a mouse, and the blastocyst is transplanted into a uterus of a recipient mouse to generate a chimeric mouse. A heterozygous mouse (F1 mouse: +/−) can be obtained by intercrossing the chimeric mouse with a wild-type mice, and a TLR6 knockout mouse of the present invention can be generated by intercrossing the heterozygous mice. In addition, as a method for confirming whether TLR6 is present in the TLR6 knockout mouse, for instance, there are Northern blotting or other such methods with which RNA isolated from the mouse obtained by the above-mentioned method is examined, and Western blotting or other such methods with which the expression of TLR6 in the mouse is examined.

It is possible to confirm that the generated TLR6 knockout mouse is unresponsive to a mycoplasma-derived lipoprotein/lipopeptide, for example, by contacting a mycoplasma-derived lipoprotein/lipopeptide with an immune cell such as a macrophage, a monocyte or a dendric cell of the TLR6 knockout mouse in vitro or in vivo, and then measuring the production amounts of TNF-á, IL-6, IL-12, IFN-ã etc. in the cells, the proliferative responses of splenic B cells, the expression amounts of antigens such as CD40, CD80, CD86 and MHC class II on the surface of splenic B cells, and the activation of molecules in signaling pathways of TLR6, such as NF-êB, JNK and IRAK. Further, the TLR6 knockout mouse of the present invention can be used as a useful model for elucidating an action mechanism of a mycoplasma-derived lipoprotein/lipopeptide and for projecting a therapeutic strategy for mycoplasma infections that cause infections such as pneumonia.

Homozygous non-human animals which were born at the expected Mendelian ratios include a deficient type being deficient in a protein that specifically recognizes a mycoplasma-derived lipoprotein/lipopeptide and its wild-type littermate, and precise comparative experiments can be conducted at an individual level by using the deficient type of homozygous non-human animals and its wild-type littermate simultaneously. Therefore, it is desirable to use a wild-type non-human animal, preferably a wild-type non-human animal which is the same species as, more preferably the littermate of, a non-human animal whose function of a gene that encodes a protein that specifically recognizes a mycoplasma-derived lipoprotein/lipopeptide is deficient on its chromosome, for instance, for the screening of an inhibitor or a promoter for a response to a mycoplasma-derived lipoprotein/lipopeptide of the present invention mentioned below.

The non-human animal model unresponsive to a mycoplasma-derived lipoprotein/lipopeptide of the present invention and an immune cell such as a macrophage, a splenocyte or a dendric cell derived from the non-human animal model can be used for the elucidation of an action mechanism of a mycoplasma-derived lipoprotein/lipopeptide, and also for screenings of an inhibitor or a promoter for mycoplasma infections such as mycoplasma pneumonia, or an inhibitor or a promoter for a response to a mycoplasma-derived lipoprotein/lipopeptide, such as an agonist or an antagonist of TLR6, etc. The method for screening the inhibitor or the promoter for mycoplasma infections such as pneumonia, or the inhibitor or the promoter for a response to a mycplasma-derived lipoprotein/lipopeptide, such as an agonist or an antagonist of TLR6, is explained with examples below.

As the method for screening an inhibitor or a promoter for a response to a mycoplasma-derived lipoprotein/lipopeptide of the present invention, a method wherein with the use of an immune cell such as a macrophage, a splenocyte or a dendric cell derived from a non-human animal model unresponsive to a mycoplasma-derived lipoprotein/lipopeptide, a subject material and a mycoplasma-derived lipoprotein/lipopeptide, a response to a mycoplasma-derived lipoprotein/lipopeptide in the immune cell is measured/evaluated, and a method wherein with the use of a non-human animal model unresponsive to a mycoplasma-derived lipoprotein/lipopeptide, a subject material and a mycoplasma-derived lipoprotein/lipopeptide, a response to a mycoplasma-derived lipoprotein/lipopeptide in the non-human animal model is measured/evaluated, etc., are exemplified.

Examples of the above-mentioned method for screening with the use of an immune cell derived from a non-human animal model unresponsive to a mycoplasma-derived lipoprotein/lipopeptide include a method comprising the steps of: contacting an immune cell obtained from a non-human animal model unresponsive to a mycoplasma-derived lipoprotein/lipopeptide with a subject material in vitro beforehand; culturing the immune cell in the presence of a mycoplasma-derived lipoprotein/lipopeptide, and measuring/evaluating a response to a mycoplasma-derived lipoprotein/lipopeptide in the immune cell, and a method comprising the steps of: contacting an immune cell obtained from a non-human animal model unresponsive to a mycoplasma-derived lipoprotein/lipopeptide with a mycoplasma-derived lipoprotein/lipopeptide in vitro beforehand; culturing the immune cell in the presence of a subject material, and measuring/evaluating a response to a mycoplasma-derived lipoprotein/lipopeptide in the immune cell.

In addition to the methods mentioned above, the following methods are exemplified: a method comprising the steps of: a subject material is administered in advance to a non-human animal model unresponsive to a mycoplasma-derived lipoprotein/lipopeptide; an immune cell obtained from the non-human animal is cultured in the presence of a mycoplasma-derived lipoprotein/lipopeptide; a response to a mycoplasma-derived lipoprotein/lipopeptide in the immune cell is measured/evaluated, and a method comprising the steps of: a subject material is administered in advance to a non-human animal model unresponsive to a mycoplasma-derived lipoprotein/lipopeptide of the present invention; the non-human animal is made to be infected with a mycoplasma-derived lipoprotein/lipopeptide; a response to a mycoplasma-derived lipoprotein/lipopeptide in an immune cell obtained from the non-human animal is measured/evaluated.

Further, a method comprising the steps of: a non-human animal model unresponsive to a mycoplasma-derived lipoprotein/lipopeptide of the present invention is made to be infected with a mycoplasma-derived lipoprotein/lipopeptide in advance; an immune cell obtained from the non-human animal is cultured in the presence of a subject material, and a response to a mycoplasma-derived lipoprotein/lipopeptide in the immune cell is measured/evaluated, and a method comprising the steps of: a non-human animal model unresponsive to a mycoplasma-derived lipoprotein/lipopeptide of the present invention is made to be infected with a mycoplasma-derived lipoprotein/lipopeptide in advance; a subject material is administered to the non-human animal, and a response to a mycoplasma-derived lipoprotein/lipopeptide in an immune cell obtained from the non-human animal is measured/evaluated are exemplified.

On the other hand, the following methods are exemplified as the method wherein with the use of a non-human animal model unresponsive to a mycoplasma-derived lipoprotein/lipopeptide of the present invention, a subject material and a mycoplasma-derived lipoprotein/lipopeptide, a response to a mycoplasma-derived lipoprotein/lipopeptide in the non-human animal model is measured/evaluated: a method comprising the steps of: a subject material is administered in advance to a non-human animal model unresponsive to a mycoplasma-derived lipoprotein/lipopeptide; the non-human animal model is made to be infected with a mycoplasma-derived lipoprotein/lipopeptide; a response to a mycoplasma-derived lipoprotein/lipopeptide in the non-human animal model is measured/evaluated, and a method comprising the steps of: a non-human animal model unresponsive to a mycoplasma-derived lipoprotein/lipopeptide is made to be infected with a mycoplasma-derived lipoprotein/lipopeptide in advance; a subject material is administered to the non-human animal model, and a response to a mycoplasma-derived lipoprotein/lipopeptide in the non-human animal model is measured/evaluated.

In the present invention, the measurement/evaluation of a response to a mycoplasma-derived lipoprotein/lipopeptide means a measurement/evaluation of a function to specifically react with a mycoplasma-derived lipoprotein/lipopeptide to transmit signals intracellularly. As such signal transmitting function, a function to produce cytokines such as TNF-á, IL-6, IL-12 and IFN-ã, a function to produce nitrite ion, a function to proliferate cells, a function to express antigens such as CD40, CD80, CD86 and MHC class II on the surface of cells, and a function to activate molecules in the signaling pathway of TLR9, such as NF-êB, JNK and IRAK are specifically exemplified, but not limited to these functions. Further, as aforementioned, in the measurement/evaluation of a response to a mycoplasma-derived lipoprotein/lipopeptide, it is preferable to evaluate the response in comparison to the measured value of a wild-type non-human animal, a wild-type non-human animal littermate in particular, as a control, because there will be no dispersion caused by individual differences.

As it is revealed by the non-human animal model specifically deficient in reactivity to a mycoplasma-derived lipoprotein/lipopeptide of the present invention that TLR6 is specifically involved in the recognition of a mycoplasma-derived lipoprotein/lipopeptide, these non-human animal models are presumed to serve as extremely useful model animals for projecting a therapeutic strategy for mycoplasma infections such as human mycoplasma pneumonia which is a primary a typical pneumonia caused by *M. pneumoniae*, bovine pleuropneumonia caused by *M. mycoides*, ovine/caprine mastitis caused by *M. agalacliae*, or chicken respiratory disease caused by *M. gallisepticum*. In addition, there is a chance that an agonist or an antagonist of TLR6 is an inhibitor or a promoter for various kinds of mycoplasma infections mentioned above, and is a useful substance for diagnosis/treatment of diseases caused by deficiency or abnormality in TLR6 activity, etc.

The present invention will be explained more specifically with examples and a reference below, but the technical scope of the present invention is not limited to these examples etc. Reference (Generation of TLR2 knockout mouse) TLR2 gene was screened from 129/SvJ mouse gene library (Stratagene) with a probe derived from a mouse EST clone (accession number D77677) which is similar to human TLR2 gene, and subcloned into a pBluescript vector (Stratagene), then characterized by restriction enzyme mapping and DNA sequencing. A targeting vector was constructed by replacing a gene fragment at an exon region 1.3 kb containing a cytoplasmic domain of a TLR2 gene with pMC1-neo (Stratagene) having Poly A signal. The targeting vector was flanked by a 4.8 kb 5' gene fragment and a 1.0 kb 3' gene fragment and contained a HSV-tk cassette at the 5' terminal. The targeting vector was linearized with SalI and electroporated into E14.1 embryonic stem cells (ES cells). ES cells being resistant to G418 and ganciclovir, and containing mutant TLR2 allele were screened from the electroporated ES cells, and the screened ES cells were microinjected into blastocysts of C57BL/6 mice to construct chimeric mice. By mating this male chimeric mouse and a female C57BL/6 mouse, TLR2 knockout mouse was constructed (Immunity 11, 443-451, 1999).

EXAMPLE 1

Generation of TLR6 Knockout Mouse

TLR6 gene was screened from 129/SvJ mouse gene library (Stratagene) with a probe derived from a mouse TLR6 gene (accession number AB020808), and subcloned into a pBluescript II SK (+) vector (Stratagene), then characterized by restriction enzyme mapping and DNA sequencing. A targeting vector was constructed by replacing a genetic site (about 6 kb) encoding an intracellular domain and a transmembrane domain of the mouse TLR6 with a neomycin-resistant gene cassette (pMC1-neo; Stratagene), and introducing a herpes simplex virus thymidine kinase (HSV-tk) as a negative selective marker (FIG. 1). The targeting vector was linearized and electroporated into E14.1 embryonic stem cells (ES cells). 126 clones being resistant to G418 and ganciclovir were selected and three clones were screened by PCR and Southern blotting.

Figure 2:
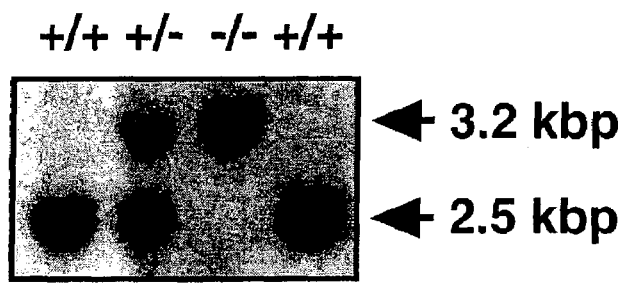
FIG. 2 is a graph showing the results of Southern blot analysis of the TLR6 knockout mice of the present invention.

Three targeted ES clones containing mutant TLR6 allele were microinjected into blastocysts of C57BL/6 mice to generate a chimeric mouse. By mating this male chimeric mouse and a female C57BL/6 mouse, a heterozygous F1 mouse was generated, and a homozygous mouse (TLR6 knockout mouse: TLR6−/−) was obtained by intercrossing the heterozygous F1 mice. Confirmation of the homozygous mouse was conducted by digesting each genomic DNA extracted from a mouse tail with EcoRI and performing Southern blotting with a probe shown in FIG. 1 (FIG. 2). The TLR6 knockout mouse (TLR6−/−) of the present invention could be generated at the expected Mendelian ratio, and did not show any obvious abnormality until it came to 25 weeks old.

EXAMPLE 2

Preparation of Peritoneal Macrophage

Each of wild-type (wild-type), TLR6 knockout (TLR6−/−) and TLR2 knockout (TLR2−/−) mice were intraperitoneally injected with 2 ml of 4% thioglycollate medium (DIFCO). Three days later, peritoneal exudate cells were isolated from the peritoneal cavity of each mouse. These cells were cultured in RPMI1640 medium (GIBCO) supplemented with 10% fetal bovine serum (GIBCO) for 2 hours at 37.degree. C. and washed with ice-cold Hank's buffered salt solution (HBSS; GIBCO) to remove nonadherent cells. Adherent cells were used as peritoneal macrophages for the following experiments.

EXAMPLE 3

Responsiveness of Macrophages Derived from TLR6 Knockout Mouse to LPS, Lipoprotein Derived from Spirochaeta and Peptidoglycan Derived from *Staphylococcus aureus*

Figure 3:
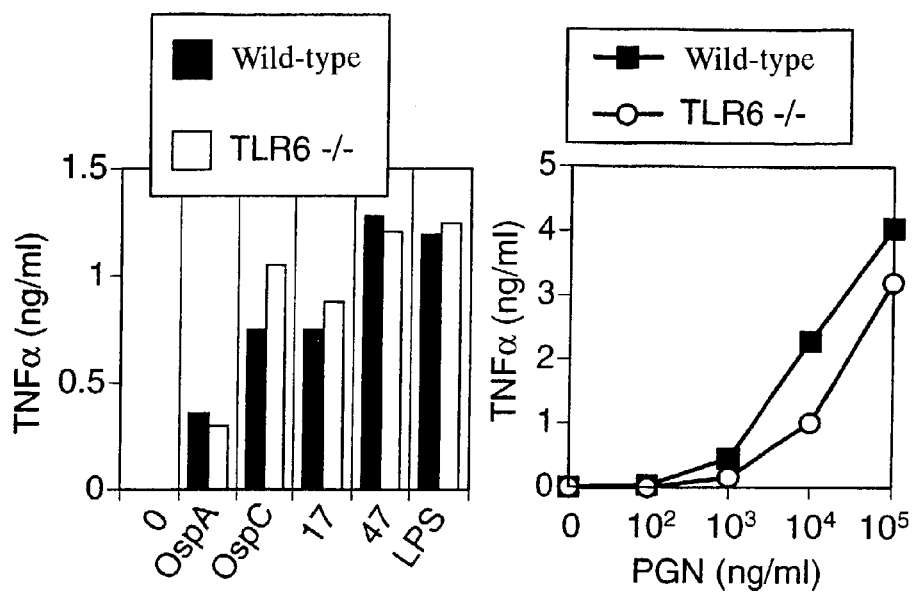
FIG. 3 is a graph showing the results of TNFá production caused by stimulation with lipoprotein, LPS or PGN in the TLR6 knockout mice and the wild-type mice of the present invention.

The present inventors have already revealed that TLR2 is indispensable for recognizing lipoprotein and peptidoglycan derived from bacteria and that TLR4 is indispensable for recognizing LPS and lipoteichoic acid by generating TLR2 and TLR4 knockout mice. Therefore, responsiveness of TLR6 knockout mouse to these LPS, lipoprotein derived from Spirochaeta, and peptidoglycan derived from *Staphylococcus aureus* was examined. Peritoneal macrophages ($5 \times 10^4$ cells) of wild-type and TLR6 knockout mice prepared in Example 2 were cultured for 24 hours together with 10 μM *B. burgdorferi*-derived lipoprotein OspA or OspC, 10 μM *T. pallidum*-derived lipoprotein 17-kDa (17) or 47-kDa (47), 100 ng/ml LPS, or various concentrations of peptidoglycan (PGN) shown in FIG. 3. When culture was completed, concentrations of TNFá in culture supernatants were measured by ELISA respectively. The results are shown in FIG. 3. These results have indicated that macrophages derived from a TLR6 knockout mouse (TLR6−/−) produce approximately the same amount of TNFá as macrophages derived from a wild-type mouse in response to OspA, OspC, 17, 47, LPS, and PGN.

EXAMPLE 4

Responsiveness of Macrophages Derived from TLR6 Knockout Mouse to Lipopeptide

Figure 4:
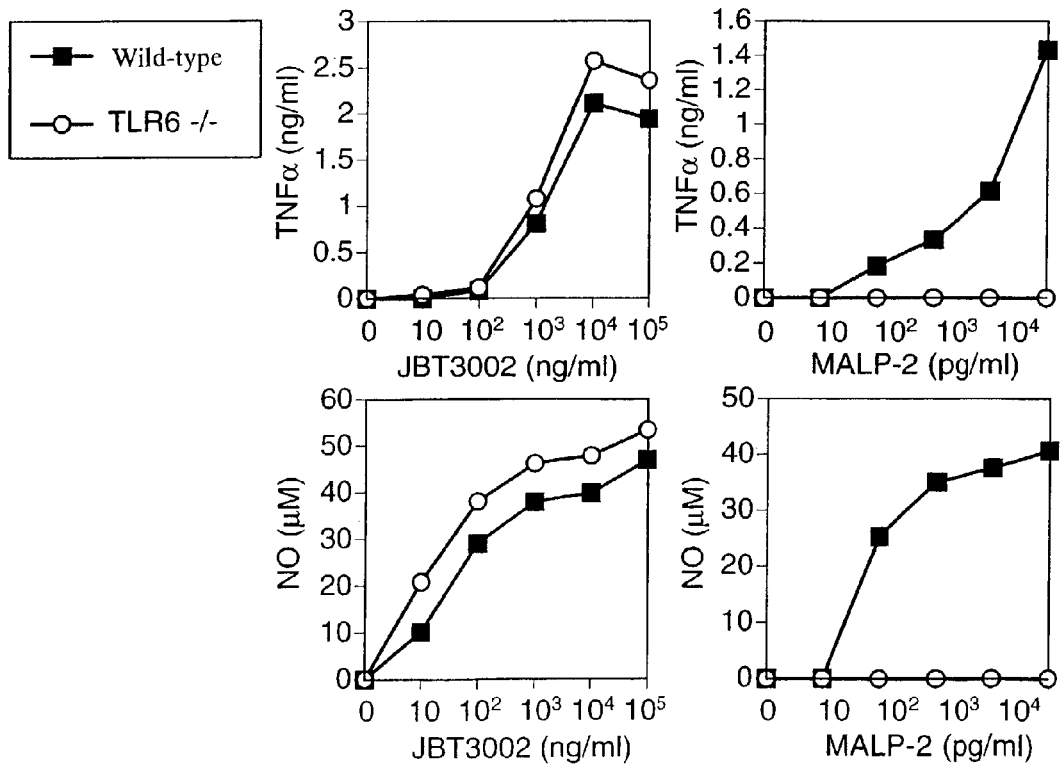
FIG. 4 is a graph showing the production of TNF-á or $NO_2^-$ caused by stimulation with lipopeptide in the TLR6 knockout mice and the wild-type mice of the present invention.

Responsiveness of peritoneal macrophages derived from a wild-type mouse or a TLR6 knockout mouse to lipopeptide was examined with synthetic Gram negative bacteria-derived lipopeptide JBT3002 and synthetic mycoplasma-derived lipopeptide MALP-2. Peritoneal macrophages ($5 \times 10^4$ cells) of wild-type and TLR6 knockout mice prepared in Example 2 were cultured for 24 hours together with various concentrations of JBT3002 (provided by Dr. Z. Dong) or MALP-2 (provided by Dr. P. F. Muhlradt) shown in FIG. 4, and stimulated. When culture was completed, the production amounts of TNF-á (TNFá) and $NO_2^-$ (NO) in culture supernatants were measured (FIG. 4). $NO_2^-$ was measured by the Greiss method using $NO_2/NO_3$ Assay Kit (Dojindo Laboratories).

The above-mentioned results indicate that: peritoneal macrophages derived from a wild-type mouse (wild-type) increased the production amounts of TNF-á (TNFá) and $NO_2^-$ (NO) in a manner dependent on doses of Gram negative bacteria-derived lipopeptide JBT3002 and mycoplasma-derived lipopeptide MALP-2, while peritoneal macrophages derived from a TLR6 knockout mouse (TLR6−/−) increased the production amounts of TNF-á and $NO_2^-$ in a manner dependent on dose of Gram negative bacteria-derived lipopeptide JBT3002 as in the case of peritoneal macrophages derived from a wild-type mouse, but produced no TNF-á and $NO_2^-$ in response to any concentrations of mycoplasma-derived lipopeptide MALP-2 (FIG. 4). From these results, it is revealed that a mycoplasma-derived lipoprotein/lipopeptide activates macrophages via TLR6.

EXAMPLE 5

Activation of Intracellular Signaling Pathway via TLR6

Figure 5:
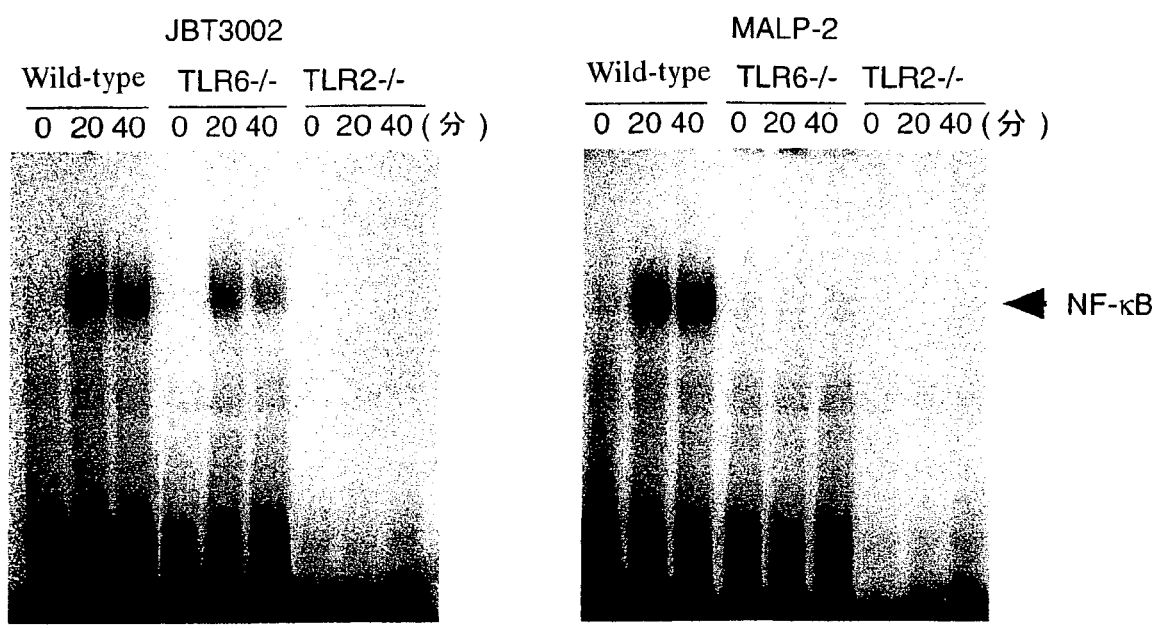
FIG. 5 is a graph showing the results of NF-êB activation caused by stimulation with lipopeptide in the TLR6 knockout mice and the wild-type mice of the present invention.

It is known that TLR signals activate IRAK, which is serine/threonine kinase, via an adapter molecule MyD88 and then activate MAP kinase and NF-êB (Immunity 11, 115-122, 1999). In addition, it is also known that a mycoplasma-derived lipoprotein/lipopeptide causes vital reaction via TLR2 and MyD88 signaling pathways (J. Immunol. 164, 554-557, 2000). Consequently, with wild-type, TLR6 knockout and TLR2 knockout mice, whether a bacteria-derived lipoprotein/lipopeptide activates intracellular signaling molecules was examined. Peritoneal macrophages ($1 \times 10^6$ cells) of wild-type (wild-type) and TLR6 knockout (TLR6−/−) and TLR2 knockout (TLR2−/−) mice prepared in Example 2 were stimulated with 0.1 ng/ml JBT3002 or 0.3 ng/ml MALP-2 for 20 or 40 minutes, and nucleoproteins were extracted from macrophages of each mouse and incubated with a specific probe containing DNA binding site of NF-êB, then subjected to electrophoresis and visualized by autoradiography (FIG. 5).

With the result that the activation of NF-êB in response to the stimulation with MALP-2 or JBT3002 was observed in macrophages derived from a wild-type mouse. In macrophages derived from a TLR6 knockout mouse, though no activation in response to MALP-2 was observed, activation in response to JBT3002 was observed. Further, in macrophages derived from a TLR2 knockout mouse, no activation was observed in response to MALP-2 and JBT3002. These findings have revealed that TLR6 is specifically involved in the recognition of a mycoplasma-derived lipoprotein/lipopeptide. In addition, it is presumed that both TLR6 and TLR2 are indispensable for recognizing a mycoplasma-derived lipoprotein/lipopeptide, and that these two molecules form a heterodimer to transmit mycoplasma-derived lipoprotein/lipopeptide signals.

INDUSTRIAL APPLICABILITY

The non-human animal model unresponsive to a mycoplasma-derived lipoprotein/lipopeptide of the present invention such as a TLR6 knockout mouse is unresponsive only to a mycoplasma-derived lipoprotein/lipopeptide. Therefore, the use of this non-human animal model makes it possible to screen an inhibitor or a promoter for mycoplasma infections such as mycoplasma pneumonia, or an inhibitor or a promoter for responsiveness to a mycoplasma-derived lipoprotein/lipopeptide such as an agonist or an antagonist of TLR6, and moreover, to obtain novel information useful for elucidating a molecular mechanism of the occurrence of infections caused by bacteria including Mycoplasma.

The invention claimed is:

1. A transgenic mouse whose genome comprises a homozygous disruption of the TLR-6 gene, said TLR-6 gene encoding a polypeptide that recognizes a MALP-2 mycoplasma-derived lipoprotein/lipopeptide, wherein macrophage cells isolated from the transgenic mouse are unresponsive to MALP-2.

2. A macrophage cell isolated from a transgenic mouse whose genome comprises a homozygous disruption of the TLR-6 gene, said TLR-6 gene encoding a polypeptide that recognizes a MALP-2 mycoplasma-derived lipoprotein/lipopeptide, wherein the macrophage cell is unresponsive to MALP-2.

* * * * *